(12) United States Patent
Takeuchi et al.

(10) Patent No.: US 10,960,859 B2
(45) Date of Patent: Mar. 30, 2021

(54) AUTOMATIC BRAKE CONTROL APPARATUS AND COMPUTER-READABLE NON-TRANSITORY STORAGE MEDIUM

(71) Applicant: DENSO CORPORATION, Kariya (JP)

(72) Inventors: Tetsuichi Takeuchi, Kariya (JP); Takahiko Naruse, Kariya (JP); Tomoaki Mizuno, Kariya (JP); Toshiya Takeuchi, Kariya (JP); Takehito Teramae, Kariya (JP); Ichiro Yoshida, Kariya (JP); Takafumi Ito, Kariya (JP)

(73) Assignee: DENSO CORPORATION, Kariya (JP)

( * ) Notice: Subject to any disclaimer, the term of this patent is extended or adjusted under 35 U.S.C. 154(b) by 219 days.

(21) Appl. No.: 16/086,369

(22) PCT Filed: Jan. 16, 2017

(86) PCT No.: PCT/JP2017/001219
§ 371 (c)(1),
(2) Date: Sep. 19, 2018

(87) PCT Pub. No.: WO2017/168955
PCT Pub. Date: Oct. 5, 2017

(65) Prior Publication Data
US 2019/0100175 A1    Apr. 4, 2019

(30) Foreign Application Priority Data
Mar. 29, 2016    (JP) .............................. JP2016-065643

(51) Int. Cl.
*B60T 7/12* (2006.01)
*G08G 1/16* (2006.01)
(Continued)

(52) U.S. Cl.
CPC ............ *B60T 7/12* (2013.01); *A61B 5/14553* (2013.01); *A61B 5/18* (2013.01); *B60T 8/171* (2013.01);
(Continued)

(58) Field of Classification Search
CPC ........... B60T 2201/022; B60T 2210/32; B60T 2220/02; B60T 7/12; B60T 8/171;
(Continued)

(56) References Cited

U.S. PATENT DOCUMENTS

| 2009/0069994 | A1 | 3/2009 | Uechi et al. | |
| 2010/0241021 | A1* | 9/2010 | Morikawa | A61B 5/048 600/544 |
| 2016/0001781 | A1* | 1/2016 | Fung | G16H 50/20 701/36 |

FOREIGN PATENT DOCUMENTS

| JP | 2008037201 A | 2/2008 |
| JP | 2009-018625 A | 1/2009 |

(Continued)

OTHER PUBLICATIONS

Fukui et al. (JP 2011248535) (see attached PDF version of machine translation provided by Espacenet) (Year: 2011).*

*Primary Examiner* — Michael V Kerrigan
(74) *Attorney, Agent, or Firm* — Harness, Dickey & Pierce, P.L.C.

(57) ABSTRACT

An automatic brake control apparatus controls a braking device of a vehicle to execute a brake operation at a brake operating timing. The automatic brake control apparatus includes a brain activity state acquirer unit configured to acquire an activity state of a brain of a driver of the vehicle; a change determiner unit configured to use the activity state of the brain of the driver acquired after the braking device has executed a brake operation at a brake operating timing to determine whether changing the brake operating timing is (Continued)

| | | STRESS DEGREE | |
|---|---|---|---|
| | | LOW | HIGH |
| COMFORT DEGREE | COMFORT | COMFORTABLE NOT CHANGING BRAKE OPERATING TIMING | SETTING BRAKE OPERATING TIMING ONE LEVEL EARLIER |
| | UNCOMFORTABLE | SETTING BRAKE OPERATING TIMING ONE LEVEL LATER | SETTING BRAKE OPERATING TIMING TWO LEVELS EARLIER | necessary or unnecessary; and a change controller configured to change the brake operating timing in response to that changing the brake operating timing is determined to be necessary.

11 Claims, 4 Drawing Sheets

(51) Int. Cl.
  *A61B 5/18* (2006.01)
  *B60T 8/171* (2006.01)
  *A61B 5/1455* (2006.01)
  *B60W 40/08* (2012.01)
  *G06F 3/01* (2006.01)
  *A61B 5/01* (2006.01)
  *A61B 5/00* (2006.01)
  *A61B 5/021* (2006.01)

(52) U.S. Cl.
  CPC ............ *B60W 40/08* (2013.01); *G06F 3/015* (2013.01); *G08G 1/16* (2013.01); *G08G 1/166* (2013.01); *A61B 5/0075* (2013.01); *A61B 5/01* (2013.01); *A61B 5/021* (2013.01); *A61B 5/6893* (2013.01); *B60T 2201/022* (2013.01); *B60T 2210/32* (2013.01); *B60T 2220/02* (2013.01); *B60W 2040/0872* (2013.01); *B60W 2540/22* (2013.01)

(58) Field of Classification Search
  CPC ........... A61B 5/18; A61B 5/01; A61B 5/0075; A61B 5/6893; A61B 5/021; A61B 5/163; G06F 3/015; B60W 40/08; B60W 2040/0872; B60W 2540/22; B60W 2050/0089; B60W 2040/0818; G08G 1/163; G08G 1/165; G08G 1/16; G08G 1/166
  See application file for complete search history.

(56) References Cited

FOREIGN PATENT DOCUMENTS

| | | |
|---|---|---|
| JP | 2010038821 A | 2/2010 |
| JP | 2011238133 A | 11/2011 |
| JP | 2011248535 A | 12/2011 |
| JP | 2012-006505 A | 1/2012 |
| JP | 2015176447 A | 10/2015 |
| JP | 2016-013753 A | 1/2016 |
| JP | 2016-020177 A | 2/2016 |

* cited by examiner

|  |  | STRESS DEGREE | |
|---|---|---|---|
|  |  | LOW | HIGH |
| COMFORT DEGREE | COMFORT | COMFORTABLE NOT CHANGING BRAKE OPERATING TIMING | SETTING BRAKE OPERATING TIMING ONE LEVEL EARLIER |
|  | UNCOMFORTABLE | SETTING BRAKE OPERATING TIMING ONE LEVEL LATER | SETTING BRAKE OPERATING TIMING TWO LEVELS EARLIER |

AUTOMATIC BRAKE CONTROL APPARATUS AND COMPUTER-READABLE NON-TRANSITORY STORAGE MEDIUM

CROSS REFERENCE TO RELATED APPLICATIONS

This application is a U.S. National Phase Application under 35 U.S.C. 371 of International Application No. PCT/JP2017/001219 filed on Jan. 16, 2017. The present application is based on and claims the benefit of priority from Japanese Patent Application No. 2016-065643 filed on Mar. 29, 2016. The entire disclosures of all of the above applications are incorporated herein by reference.

TECHNICAL FIELD

The present disclosure relates to an automatic brake control apparatus and a computer program.

BACKGROUND ART

There is provided an automatic brake control apparatus to control a braking device to execute a brake operation for a purpose of preventing a collision with an obstacle such as a preceding vehicle or a pedestrian or for a purpose of causing the vehicle to transition to be at a safety speed (for example, refer to Patent literature 1).

PRIOR ART LITERATURES

Patent Literature

Patent literature 1: JP 2015-176447 A

SUMMARY OF INVENTION

This kind of automatic brake control apparatus controls the braking device in order to stop the vehicle in cases that maintaining the vehicle speed constant (that is, going along with the situation) may involve a collision with an obstacle. In this case, this kind of automatic brake control apparatus usually controls the braking device to execute a brake operation at a brake operating timing which can provide a safety allowance, instead of controlling the braking device to execute a brake operation at a marginal brake operating timing that causes the vehicle to stop just before the obstacle. Moreover, in cases that the vehicle accelerates to increase the vehicle speed, this kind of automatic brake control apparatus controls the braking device to execute a brake operation at a brake operating timing when the vehicle speed reaches a caution speed, thereby allowing the vehicle speed to transition to a safety speed. In the above, when the safety allowance or the caution speed is fixed, some drivers sense that the performance of the brake is too slow or too early.

It is an object of the present disclosure to provide an automatic brake control apparatus and a computer program, which enables a braking device to be controlled to execute a brake operation at a brake operating timing which a driver likes while enhancing a comfort in driving.

According to an example of the present disclosure, a brain activity state acquirer unit acquires an activity state of a brain of a driver. A change determiner unit uses the activity state of the brain of the driver acquired after a braking device has executed a brake operation at a brake operating timing to determine whether changing the brake operating timing is necessary or unnecessary. A change controller changes the brake operating timing in response to that changing the brake operating timing is determined to be necessary.

That is, the activity state of the brain of the driver is acquired after a brake operation has been executed by the controlled braking device at a brake operating timing; by using the acquired activity state of the brain, either a necessity or an unnecessity of changing the brake operating timing is determined. The change in the activity state of the brain of the driver takes place due to the fact that the brake operation has been executed by the controlled braking device. That change can be used to change the brake operating timing. This configuration enables the braking device to be controlled to execute a brake operation at a brake operating timing which the driver likes while enhancing a comfort in driving the vehicle.

BRIEF DESCRIPTION OF DRAWINGS

The above and other objects, features and advantages of the present disclosure will become more apparent from the following detailed description made with reference to the accompanying drawings. In the drawings.

EMBODIMENTS FOR CARRYING OUT INVENTION

Figure 1:
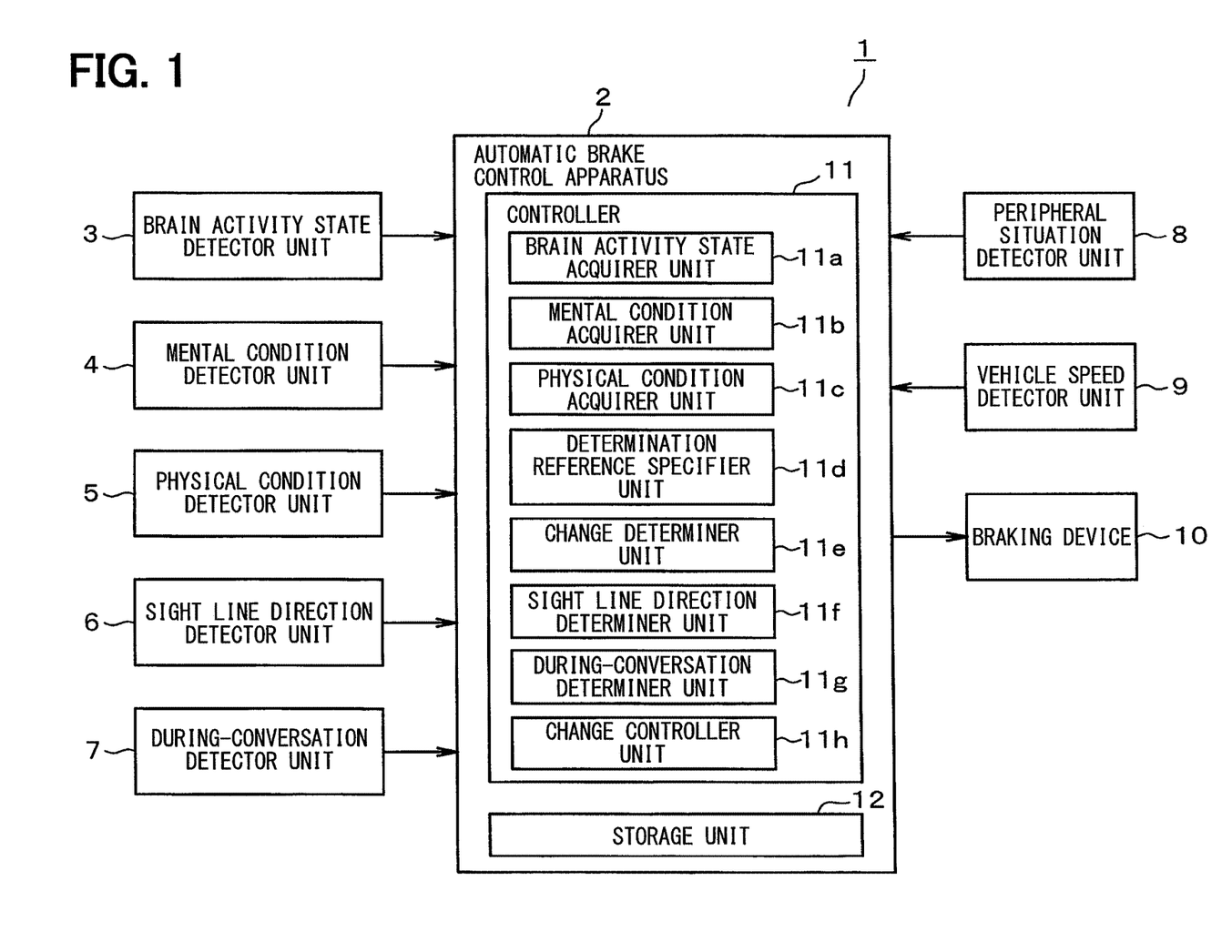
FIG. 1 is a functional block diagram illustrating an embodiment.

The following explains an embodiment of the present disclosure with reference to the drawings. An automatic brake control system 1 includes an automatic brake control apparatus 2, a brain activity state detector unit 3, a mental condition detector unit 4, a physical condition detector unit 5, a sight line direction detector unit 6, a during-conversation detector unit 7, a peripheral situation detector unit 8, a vehicle speed detector unit 9, and a braking device 10. The automatic brake control apparatus 2 controls the output of a brake operating signal to the braking device 10 by using respective detection signals inputted from the detector units 3 to 9.

The brain activity state detector unit 3 detects the activity state of the driver's brain using a technology of NIRS (Near Infra-Red Spectroscopy). In the information processing of the brain, two systems of an information distributing system performed by the nervous activity and an energy supplying system supporting the nervous activity are closely related. The nervous activity takes place so that the neighboring blood vessel extends to execute the adjustment mechanism which provides much arterial blood containing the glucose or the oxygen used as the energy source. It is assumed that the blood flow volume and blood volume increase in the tissue near the active nerve to change the oxidation state of the blood (that is, the ratio of oxyhemoglobin concentration and deoxyhemoglobin concentration). Such relation between the nervous activity and the brain blood reaction is referred to as a neurovascular coupling. Based on the assumption that the neurovascular coupling is present, the technology of NIRS detects the activity state of the driver's brain by detecting the partial hemoglobin concentration in the brain.

In detail, the brain activity state detector unit 3 radiates the near-infrared light on the driver's scalp, and receives the irregularly reflected near-infrared light. The near-infrared light radiated on the driver's scalp has the high living body permeability which transmits the skin and the bone; thereby, the light component of the near-infrared light diffuses in the brain tissue, reaching the cerebral cortex which is in the about 20-30 mm deep from on the scalp. The oxyhemoglobin concentration and the deoxyhemoglobin concentration in the blood have mutually different optical absorption properties; this difference enables the detection of the light component which is irregularly reflected at the point distant from the irradiation point by several centimeters. By detecting the light component as the above, the brain activity state detector unit 3 estimates the change in the oxyhemoglobin concentration and the deoxyhemoglobin concentration of the cerebral cortex, detecting the activity state of the driver's brain. Further, in addition to the oxyhemoglobin concentration and the deoxyhemoglobin concentration of the cerebral cortex, the brain activity state detector unit 3 may also estimate the change in the total hemoglobin concentration that is the total of the oxyhemoglobin concentration and the deoxyhemoglobin concentration, detecting the activity state of the driver's brain. Upon detecting the activity state of the driver's brain, the brain activity state detector unit 3 outputs the detection signal which indicates the detection result to the automatic brake control apparatus 2.

The mental condition detector unit 4 detects whether the driver's mental condition is in a manic-depressive state, for instance, and outputs a detection signal which indicates such a detection result to the automatic brake control apparatus 2. The physical condition detector unit 5 detects the driver's physical condition with the body temperature, the heart rate, the pulse rate of the driver, etc., and outputs a detection signal which indicates such a detection result to the automatic brake control apparatus 2.

The sight line direction detector unit 6 is configured to include a driver capturing camera which captures an image of an upper half body of a driver who is seated on a driver seat. The sight line direction detector unit 6 analyzes the movement of the head or eyeballs of the driver from the image captured by the driver capturing camera to detect a sight line direction of the driver, outputting a detection signal which indicates the detection result to the automatic brake control apparatus 2. It is noted that the driver capturing camera may include a CCD (Charge Coupled Device) image sensor, or a CMOS (Complementary Metal Oxide Semiconductor) image sensor, and may include one camera unit or a plurality of camera units.

The during-conversation detector unit 7 is configured to include a speaker which collects speeches uttered by occupants including the driver. The during-conversation detector unit 7 analyzes the collected speeches to detect whether the driver is during a conversation with an occupant, outputting a detection signal which indicates the detection result to the automatic brake control apparatus 2.

The peripheral situation detector unit 8 is configured to include a vehicle periphery capturing camera which captures an image of a vehicle periphery surrounding the vehicle, a LADAR (Laser Detection and Ranging), and a LIDAR (Light Detection and Ranging). The vehicle periphery capturing camera, the LADAR, and the LIDAR are arranged in a vehicle-body front region, a vehicle-body rear region, a vehicle-body left region, or a vehicle-body right region, for example. The peripheral situation detector unit 8 analyzes images captured by the vehicle periphery capturing camera or sensor signals from the LADAR or the LIDAR, to detect the situation of the vehicle periphery, outputting a detection signal which indicates the detection result to the automatic brake control apparatus 2. The peripheral situation detector unit 8 detects a distance from the vehicle to an obstacle and a present safety speed as a vehicle periphery situation. It is noted that the peripheral situation detector unit 8 may cooperate with a navigation system to detect a vehicle periphery situation from the various kinds of traffic information, such as a road class or a distance up to an intersection.

The vehicle speed detector unit 9 is configured to include a speed sensor. The vehicle speed detector unit 9 detects a vehicle speed and outputs a detection signal which indicates a detection result to the automatic brake control apparatus 2. The braking device 10 executes a brake operation upon receiving a brake operating signal from the automatic brake control apparatus 2.

The automatic brake control apparatus 2 includes a controller 11 and a storage unit 12. The controller 11 is configured by a microcomputer having a CPU (Central Processing Unit), a ROM (Read-Only Memory), a RAM (Random Access Memory), and an I/O (Input/Output). The controller 11 executes a computer program stored in a non-transitory tangible storage medium to perform a process corresponding to the computer program and control an overall operation of the automatic brake control apparatus 2.

The controller 11 includes a brain activity state acquirer unit 11*a*, a mental condition acquirer unit 11*b*, a physical condition acquirer unit 11*c*, a determination reference specifier unit 11*d*, a change determiner unit 11*e*, a sight line direction determiner unit 11*f*, a during-conversation determiner unit 11*g*, and a change controller 11*h*. Each of the units 11*a* to 11*h* is configured by a computer program executed by the controller 11 and is achieved with software.

The brain activity state acquirer unit 11*a* acquires an activity state of a brain of the driver from a detection signal inputted from the brain activity state detector unit 3. The mental condition acquirer unit 11*b* acquires a mental condition of the driver from a detection signal inputted from the mental condition detector unit 4. The physical condition acquirer unit 11*c* acquires a physical condition of the driver from a detection signal inputted from the physical condition detector unit 5. The determination reference specifier unit 11*d* specifies a determination reference for determining an activity state of the brain of the driver from the mental condition acquired by the mental condition acquirer unit 11*b* and the physical condition acquired by the physical condition acquirer unit 11*c*.

The change determiner unit 11*e* determines a necessity or an unnecessity of changing a brake operating timing by comparing the above-mentioned determination reference with a comfort degree and a stress degree as the activity state of the brain of the driver acquired by the brain activity state acquirer unit 11*a*. The sight line direction determiner unit 11*f* determines the sight line direction of the driver from a detection signal inputted from the sight line direction detector unit 6. The during-conversation determiner unit 11*g* determines whether the driver is during a conversation from a detection signal inputted from the during-conversation detector unit 7. The change controller 11*h* changes a brake operating timing in response to that the change determiner unit 11*e* determines the necessity of changing the brake operating timing.

Figure 2:
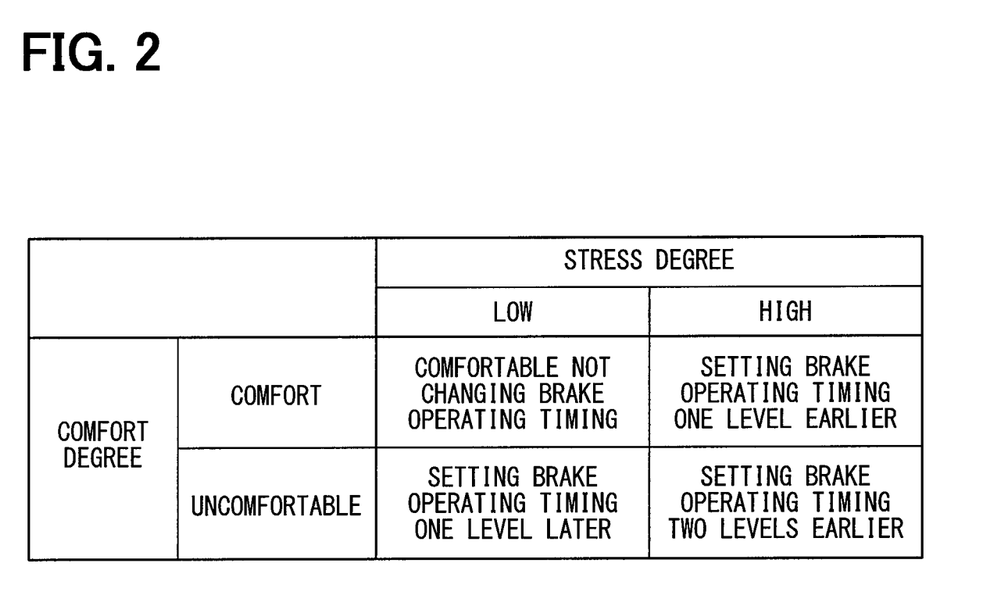
FIG. 2 is a diagram illustrating a list of variable modes of a brake operating timing.

The storage unit 12 stores a mental condition and a physical condition of the driver, and a brake operating timing while storing a list illustrating the variable modes of the brake operating timing, as in FIG. 2. The list classifies the brake operating timing into four modes based on combinations of a comfort degree and a stress degree; the four modes include not changing the brake operating timing; setting the brake operating timing one level earlier; setting the brake operating timing one level later; and setting the brake operating timing two levels earlier.

Figure 3:
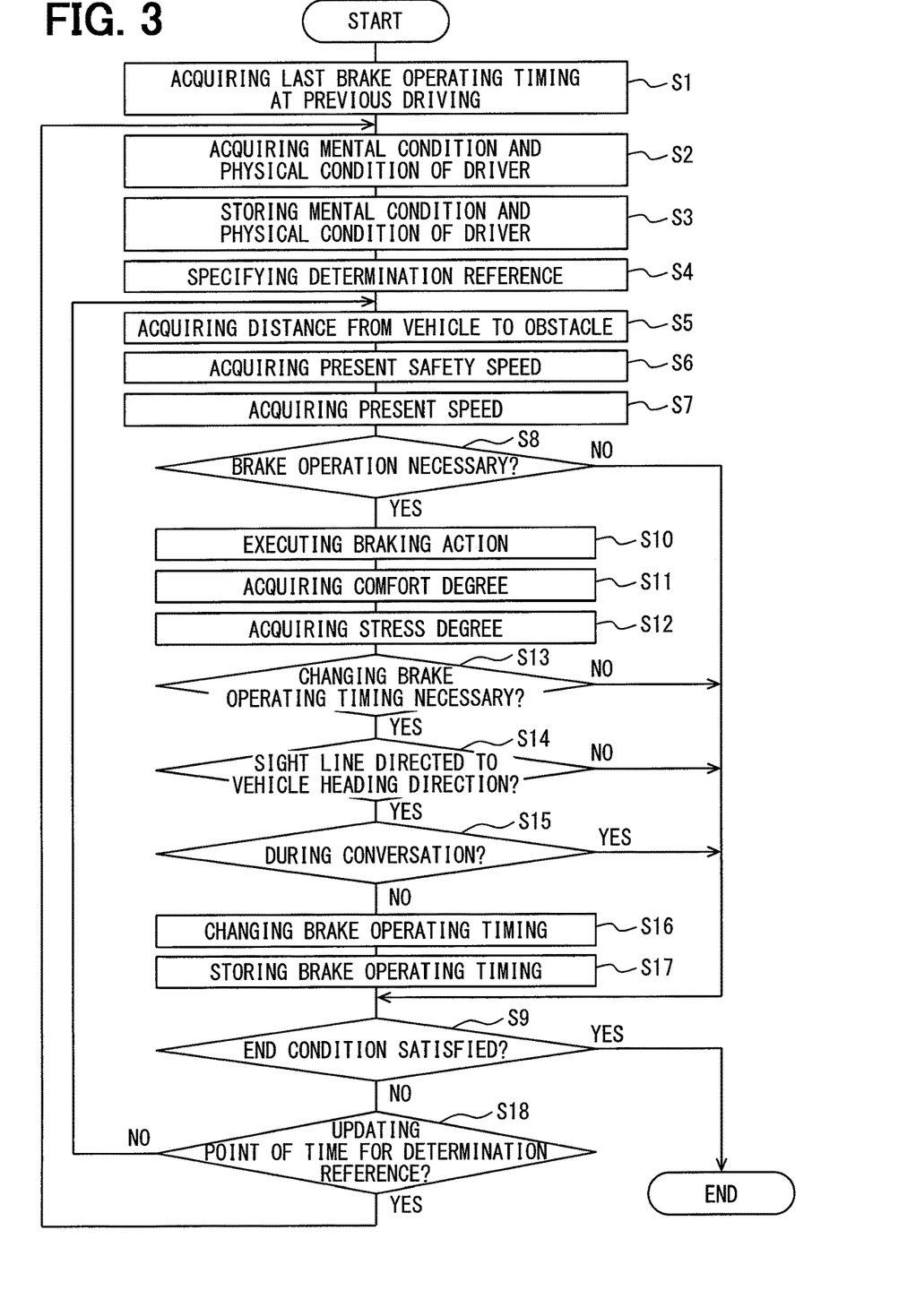
FIG. 3 is a flowchart.
Figure 4:
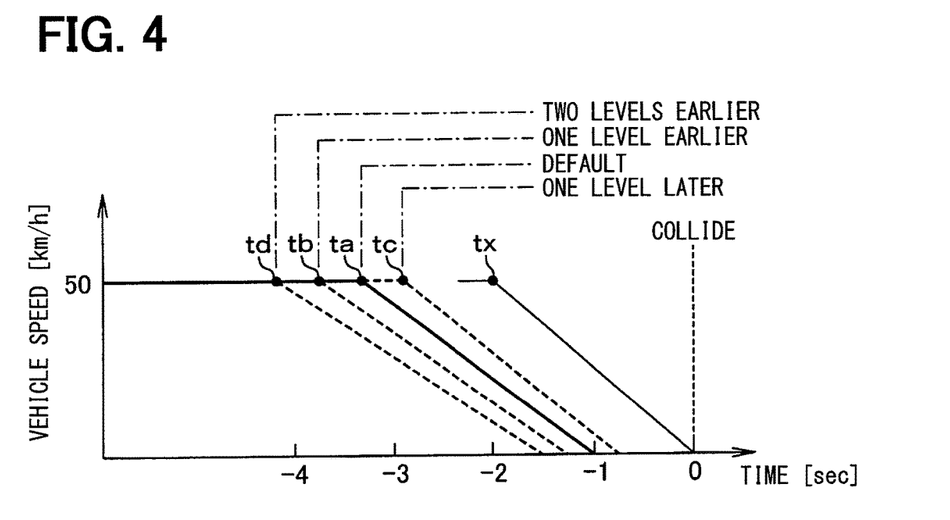
FIG. 4 is a diagram illustrating variable modes of a brake operating timing (part 1)
Figure 5:
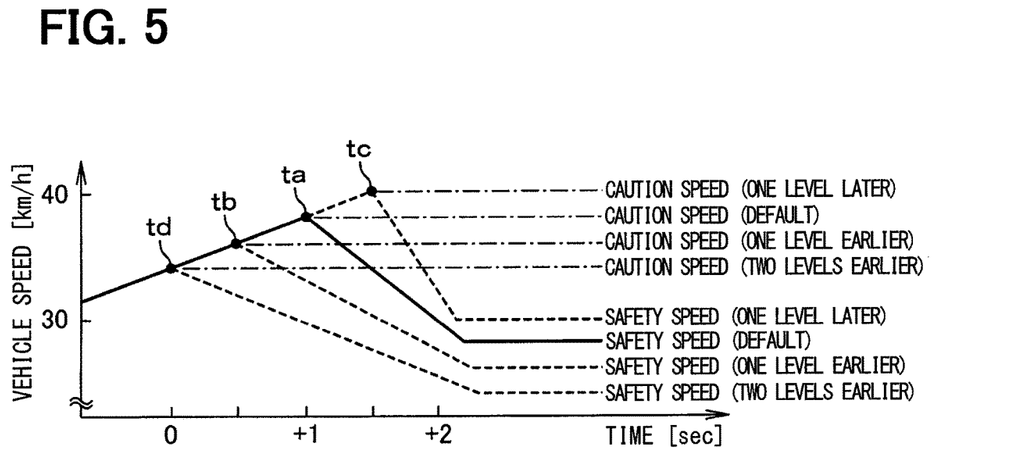
FIG. 5 is a diagram illustrating variable modes of a brake operating timing (part 2).

The following explains operations in the above configuration with reference to FIGS. 3 to 5. The controller 11 performs an automatic brake control process. The controller 11 starts an automatic brake control process in response to that a start condition of starting the automatic brake control process is satisfied, such that an ignition switch switches from OFF to ON, for example. It is noted that the controller 11 may regard, as a start condition, a vehicle speed being equal to or greater than a predetermined speed or a predetermined manipulation made by the driver.

With the start of the automatic brake control process, the controller 11 acquires a last brake operating timing that is employed at a previous driving operation and stored in the storage unit 12 (S1). The controller 11 causes the mental condition acquirer unit 11b to acquire a mental condition of the driver by using a detection signal inputted from the mental condition detector unit 4, while causing the physical condition acquirer unit 11c to acquire a physical condition of the driver by using a detection signal inputted from the physical condition detector unit 5 (S2). The controller 11 stores the mental condition and the physical condition of the driver in the storage unit 12 (S3). The controller 11 causes the determination reference specifier unit 11d to specify a determination reference for determining the activity state of the brain of the driver by using the mental condition and the physical condition of the driver which are stored (S4).

The controller 11 acquires a distance from the vehicle to an obstacle and a present safety speed by using detection signals inputted from the peripheral situation detector unit 8 (S5, S6), and acquires a present vehicle speed by using a detection signal inputted from the vehicle speed detector unit 9 (S7). The controller 11 causes the change determiner unit 11e to determine a necessity or an unnecessity of a brake operation by using the distance from the vehicle to the obstacle, the present safety speed, and the present vehicle speed (S8). When determining the unnecessity of a brake operation (S8: NO), the controller 11 determines whether an end condition of ending the automatic brake control process is satisfied (S9). In contrast, when determining that a brake operation is necessary in order to prevent the vehicle from colliding with an obstacle such as a preceding vehicle or a pedestrian or to control the vehicle to transition to be at a safety speed (S8: YES), the controller 11 outputs a brake operating signal to the braking device 10 to control the braking device 10 to execute a brake operation (S10).

After controlling the braking device 10, the controller 11 acquires a comfort degree and a stress degree as an activity state of the brain of the driver by using detection signals inputted from the brain activity state detector unit 3 (S11, S12, and equivalent to a brain activity state acquiring step). The controller 11 determines a necessity or an unnecessity of changing the brake operating timing by using the comfort degree and the stress degree (S13 and equivalent to a change determining step). That is, the controller 11 uses the list stored in the storage unit 12 to thereby select one of four modes as follows: not changing the brake operating timing; setting the brake operating timing one level earlier; setting the brake operating timing one level later; and setting the brake operating timing two levels earlier.

When determining that the comfort degree is comfortable and the stress degree is low, the controller 11 determines the unnecessity of changing the brake operating timing. That is, when determining that the comfort degree is comfortable and the stress degree is low, the controller 11 determines that the brake operation was executed at a brake operating timing which the driver likes, determining that changing the brake operating timing is unnecessary. When determining that changing the brake operating timing is unnecessary (S13: NO), the controller 11 determines also whether an end condition of ending the automatic brake control process is satisfied (S9).

In contrast, when determining that the comfort degree is comfortable but the stress degree is high, the controller 11 determines that the brake operating timing needs to be set to be one level earlier. That is, when determining that the comfort degree is comfortable but the stress degree is high, the controller 11 determines that the brake operating timing is slightly late, determining that the brake operating timing needs to be set to be one level earlier. Further, when determining that the comfort degree is uncomfortable and simultaneously the stress degree is low, the controller 11 determines that the brake operating timing needs to be set to be one level later. That is, when determining that the comfort degree is uncomfortable and simultaneously the stress degree is low, the controller 11 determines that the brake operating timing is slightly early, determining that the brake operating timing needs to be set to be one level later. Further, when determining that the comfort degree is uncomfortable and simultaneously the stress degree is high, the controller 11 determines that the brake operating timing needs to be set to be two levels earlier. That is, when determining that the comfort degree is uncomfortable and simultaneously the stress degree is high, the controller 11 determines that the brake operating timing is significantly late, determining that the brake operating timing needs to be set to be two levels earlier.

When determining that changing the brake operating timing is necessary (S13: YES), the controller 11 causes the sight line direction determiner unit 11f to determine whether the sight line of the driver is directed to the heading direction of the vehicle by using a detection signal inputted from the sight line direction detector unit 6 (S14). When determining that the sight line of the driver is not directed to the heading direction (S14: NO), the controller 11 determines whether an end condition of ending the automatic brake control process is satisfied (S9). That is, the driver's sight line direction is not the heading direction of the vehicle. This signifies that the driver fails to recognize whether or not a brake operation is executed to thereby pose a high possibility that any result of the brake operation is not reflected in the activity state of the brain. The controller 11 thus does not change the brake operating timing thereafter.

When determining that the driver's sight line direction is the heading direction of the vehicle (S14: YES), the controller 11 determines whether the driver is during a conversation by using a detection signal inputted from the during-conversation detector unit 7 (S15). When determining that the driver is during a conversation (S15: YES), the controller 11 determines also whether an end condition of ending the automatic brake control process is satisfied (S9). That is, the driver is during a conversation with a fellow passenger. This signifies that the driver fails to recognize whether or not a brake operation is executed to thereby pose a high possibility that any result of the brake operation is not reflected in the activity state of the brain. The controller 11 thus does not change the brake operating timing thereafter.

When determining that the driver is not during a conversation (S15: NO), the controller 11 changes the brake operating timing into one of three modes selected previously from the list (S16 and equivalent to a change controlling step). The three modes are as follows: setting the brake operating timing one level earlier; setting the brake operating timing one level later; and setting the brake operating timing two levels earlier. When changing the brake operating timing, the controller 11 stores the changed brake operating timing in the storage unit 12 (S17), and determines whether an end condition of ending the automatic brake control process is satisfied (S9).

When determining that an end condition of ending the automatic brake control process is not satisfied (S9: NO), the controller 11 determines whether it is, of updating the determination reference, an updating point of time that is predetermined with given intervals (S18). When determining that it is not an updating point of time (S18: NO), the controller 11 returns to Step S5 to repeat the processing after Step S5. When determining that it is an updating point of time (S18: YES), the controller 11 returns to Step S2 to repeat the processing after Step S2. In contrast, when determining that an end condition of ending the automatic brake control process is satisfied such that an ignition switch switches from ON to OFF (S9: YES), for example, the controller 11 ends the automatic brake control process.

By performing a series of processing as explained above, the controller 11 changes the brake operating timing as follows. The situation of performing an automatic brake control includes a situation intending to prevent the vehicle from colliding with an obstacle such as a preceding vehicle or a pedestrian, and a situation intending to cause the vehicle speed to transition to a safety speed. The following explains the respective situations.

(1) Situation Intending to Prevent the Vehicle from Colliding with an Obstacle

With reference to FIG. 4, in cases that maintaining the vehicle speed constant (that is, going along with the situation) may pose a collision with an obstacle, the controller 11 controls the braking device 10 to execute a brake operation in order to stop the vehicle. The braking device 10 is controlled to execute a brake operation usually at a default brake operating timing ("ta" in FIG. 4) providing a safety allowance, instead of the braking device 10 being controlled to execute a brake operation at a marginal brake operating timing ("tx" in FIG. 4) enabling the vehicle to stop just before the obstacle.

When determining that the comfort degree is comfortable and simultaneously the stress degree is low as an activity state of the brain of the driver after the controlled braking device 10 has executed a brake operation, the controller 11 determines that changing the brake operating timing is unnecessary and continues maintaining the brake operating timing to be a default brake operating timing.

In contrast, when determining that the comfort degree is comfortable but the stress degree is high after the brake operation has been executed, the controller 11 determines that the brake operating timing needs to be set to be one level earlier and changes the brake operating timing from "ta" to "tb" in FIG. 4, so as to reduce the stress degree after the brake operation is executed at the next brake operating timing. Further, when determining that the comfort degree is uncomfortable and simultaneously the stress degree is low, the controller 11 determines that the brake operating timing needs to be set to be one level later and changes the brake operating timing from "ta" to "tc" in FIG. 4, so as to make the comfort degree comfortable after the brake operation is executed at the next brake operating timing. Further, when determining that the comfort degree is uncomfortable and simultaneously the stress degree is high, the controller 11 determines that the brake operating timing needs to be set to be two levels earlier and changes the brake operating timing from "ta" to "td" in FIG. 4, so as to reduce the stress degree and simultaneously make the comfort degree comfortable after the brake operation is executed at the next brake operating timing.

The following describes an example of a specific numerical value where the vehicle travels at a constant vehicle speed of 50 km/h. The controller 11 performs the automatic brake control at the brake operating timing of default, which is 1.33 second earlier than the marginal brake operating timing, while setting the deceleration for speed reduction to 6.01 m/s^2 (the second power of s) which is slower than 6.94 m/s^2 which is the marginal deceleration. The controller 11 performs the automatic brake control at the brake operating timing one level later, which is 0.9 second earlier than the marginal brake operating timing, while setting the deceleration for speed reduction to 6.47 m/s^2 which is slower than 6.94 m/s^2 which is the marginal deceleration. The controller 11 performs the automatic brake control at the brake operating timing one level earlier, which is 1.75 second earlier than the marginal brake operating timing, while setting the deceleration for speed reduction to 5.55 m/s^2 which is slower than 6.94 m/s^2 which is the marginal deceleration. The controller 11 performs the automatic brake control at the brake operating timing two levels earlier, which is 2.17 seconds earlier than the marginal brake operating timing, while setting the deceleration for speed reduction to 5.09 m/s^2 which is slower than 6.94 m/s^2 which is the marginal deceleration.

(2) Situation Intending to Cause the Vehicle Speed to Transition to a Safety Speed With reference to FIG. 5, in cases that the vehicle accelerates to increase the vehicle speed, the controller 11 controls the braking device 10 at a brake operating timing employed when the vehicle speed reaches a caution speed, thereby causing the vehicle speed to transition to a safety speed.

Also in this case, when determining that the comfort degree is comfortable and simultaneously the stress degree is low as an activity state of the brain of the driver after the braking device 10 is controlled to execute a brake operation, the controller 11 determines that changing the brake operating timing is unnecessary and continues maintaining the brake operating timing to be a default brake operating timing "ta" in FIG. 5.

In contrast, when determining that the comfort degree is comfortable but the stress degree is high after the brake operation has been executed, the controller 11 determines that the brake operating timing needs to be set to be one level earlier and changes the brake operating timing from "ta" to "tb" in FIG. 5, so as to reduce the stress degree after the brake operation is executed at the next brake operating timing. Further, when determining that the comfort degree is uncomfortable and simultaneously the stress degree is low, the controller 11 determines that the brake operating timing needs to be set to be one level later and changes the brake operating timing from "ta" to "tc" in FIG. 5, so as to make the comfort degree comfortable after the brake operation is executed at the next brake operating timing. Further, when determining that the comfort degree is uncomfortable and simultaneously the stress degree is high, the controller 11 determines that the brake operating timing needs to be set to be two levels earlier and changes the brake operating timing from "ta" to "td" in FIG. 5, so as to reduce the stress degree and simultaneously make the comfort degree comfortable after the brake operation is executed at the next brake operating timing.

The following describes an example of a specific numeral value where the vehicle accelerates from a vehicle speed of 20 km/h. The controller 11 performs the automatic brake control at the brake operating timing of default, which corresponds to a caution speed of 38 km/h, while setting the safety speed to 28 km/h and setting the deceleration for speed reduction to 2.31 m/s^2. The controller 11 performs the automatic brake control at the brake operating timing one level later, which corresponds to a caution speed of 40 km/h, while setting the safety speed to 30 km/h and setting the deceleration for speed reduction to 4.63 m/s^2. The controller 11 performs the automatic brake control at the brake operating timing one level earlier, which corresponds to a caution speed of 36 km/h, while setting the safety speed to 26 km/h and setting the deceleration for speed reduction to 1.59 m/s^2. The controller 11 performs the automatic brake control at the brake operating timing two levels earlier, which corresponds to a caution speed of 34 km/h, while setting the safety speed to 24 km/h and setting the deceleration for speed reduction to 1.21 m/s^2.

As explained above, the present embodiment may provide the following advantageous effects. The automatic brake control apparatus 2 determines either a necessity or an unnecessity of changing a brake operating timing by using the activity state of the brain of the driver acquired after a brake operation has been executed by the controlled braking device 10. The change in the activity state of the brain of the driver takes place due to the fact that the brake operation has been executed by the controlled braking device. That change can be used to change the brake operating timing. This configuration enables the braking device 10 to be controlled to execute a brake operation at a brake operating timing which the driver likes while enhancing a comfort in driving the vehicle.

Moreover, the automatic brake control apparatus 2 acquires a comfort degree and a stress degree as an activity state of a brain, and compares them with the determination reference, to determine either the necessity or the unnecessity of changing the brake operating timing. The change in the activity state of the brain of the driver can thus be determined by regarding the comfort degree and the stress degree as the index.

Moreover, the automatic brake control apparatus 2 acquires the mental condition and the physical condition of the driver, and specifies a determination reference by using the acquired mental condition and the physical condition of the driver; thus, the change in the activity state of the brain of the driver can be determined in consideration of the mental condition and the physical condition of the driver.

Moreover, the automatic brake control apparatus 2 updates the determination reference periodically during the driving. Even if the driver's mental condition and physical condition changes during the driving, the determination reference may thus be specified to be suitable for the change; this can determine appropriately the change in the activity state of the driver's brain.

Moreover, the automatic brake control apparatus 2 determines the necessity or the unnecessity of changing the brake operating timing for the purpose of preventing the vehicle from colliding with an obstacle and causing the vehicle to transition to be at a safety speed. The braking device 10 can be thus controlled to execute a brake operation at the brake operating timing which the driver likes under the situation intending to prevent the vehicle from colliding with an obstacle and the situation intending to cause the vehicle speed to transition to a safety speed.

Moreover, when determining that the direction of the sight line of the driver is not the heading direction of the vehicle or the driver is during a conversation even if the necessity of changing the brake operating timing is determined, the automatic brake control apparatus 2 does not change the brake operating timing. This can prevent beforehand the brake operating timing from being changed under the situation with a high possibility that the result of the executed brake operation is not reflected in the activity state of the driver's brain. The reliability in changing the brake operating timing can be thus improved.

The present disclosure is described based on the embodiment, it is understood that the present disclosure does not need to be limited to the embodiment or its configuration. The present disclosure is intended to cover various modification examples and equivalent arrangements. In addition, the various combinations and configurations, and other combinations and configurations, including more, less or only a single element, are also within the spirit and scope of the present disclosure.

The above explains an example that the comfort degree and the stress degree are acquired as the activity state of the brain to be compared with a determination reference. However, either the comfort degree or the stress degree may be acquired to be compared with a determination reference.

The above explains an example that the brake operating timing is not changed when the sight line direction of the driver is determined not to be the heading direction of the vehicle or the driver is determined to be during a conversation even if changing the brake operating timing is determined to be necessary. However, determining whether the driver's sight line direction is the heading direction of the vehicle, or determining whether the driver is during a conversation may not be necessary.

When the brake operating timing is changed, the driver may be notified of such change via displaying or speech outputting.

What is claimed is:
1. An automatic brake control apparatus that controls a braking device of a vehicle to execute a brake operation at a brake operating timing, the automatic brake control apparatus comprising:
a controller configured to
acquire a comfort degree and a stress degree as an activity state of a brain of a driver in the vehicle;
determine whether a brake operation has been executed at a brake operating timing where the comfort degree is greater than or equal to a reference comfort value and the stress degree is less than or equal to a reference stress value by using the activity state of the brain of the driver acquired after the braking device has executed the brake operation at the brake operating timing;
determine that changing the brake operating timing is necessary in response to the comfort degree being less than the reference comfort value and/or the stress degree being greater than the reference stress value; and
change the brake operating timing in response to determining that changing the brake operating timing is necessary.

2. The automatic brake control apparatus according to claim 1, wherein the controller is further configured to
acquire a mental condition of the driver; and
specify the reference comfort value and the reference stress value as a determination reference using the mental condition of the driver.

3. The automatic brake control apparatus according to claim 2, wherein the controller is further configured to update the determination reference periodically during driving of the vehicle.

4. The automatic brake control apparatus according to claim 1, wherein the controller is further configured to
acquire a physical condition of the driver; and
specify the reference comfort value and the reference stress value as a determination reference using the physical condition of the driver.

5. The automatic brake control apparatus according to claim 1, wherein the controller is further configured to determine whether changing the brake operating timing is necessary in order to avoid a collision with an obstacle.

6. The automatic brake control apparatus according to claim 1, wherein the controller is further configured to determine whether changing the brake operating timing is necessary in order to cause the vehicle to transition to be at a safety speed.

7. The automatic brake control apparatus according to claim 1, wherein
the controller is further configured to determine a direction of a sight line of the driver;
in response to determining that changing the brake operating timing is necessary and to determining that the direction of the sight line of the driver is in a heading direction of the vehicle, the controller is further configured to change the brake operating timing; and
in response to determining that the direction of the sight line of the driver is not in the heading direction of the vehicle and to determining that changing the brake operating timing is necessary, the controller is further configured to not change the brake operating timing.

8. The automatic brake control apparatus according to claim 1, wherein
the controller is further configured to determine whether the driver is having a conversation;
in response to determining that changing the brake operating timing is necessary and to determining that the driver is not having the conversation, the controller is further configured to change the brake operating timing; and
in response to determining that the driver is having the conversation and to determining that changing the brake operating timing is necessary, the controller is further configured to not change the brake operating timing.

9. The automatic brake control apparatus according to claim 1, wherein the controller is further configured to
determine whether an ending condition that ends an automatic brake control process is satisfied;
determine whether the brake operation is necessary;
update a determination reference that includes the reference comfort value and the reference stress value; and
in response to determining that the ending condition is not satisfied and that the brake operation is necessary, continue determining whether changing the brake operating timing is necessary from a time after updating the determination reference until determining that the brake operation is unnecessary.

10. A computer-readable non-transitory storage medium storing a computer program including instructions causing a controller of an automatic brake control apparatus that controls a braking device of a vehicle to execute a brake operation at a brake operating timing, the instructions comprising:
acquiring a comfort degree and a stress degree as an activity state of a brain of a driver of the vehicle;
determining whether a brake operation has been executed at a brake operating timing where the comfort degree is greater than or equal to a reference comfort value and the stress degree is less than or equal to a reference stress value by using the activity state of the brain of the driver acquired after the braking device has executed the brake operation at the brake operating timing;
determine that changing the brake operating timing is necessary in response to the comfort degree being less than the reference comfort value and/or the stress degree being greater than the reference stress value; and
changing the brake operating timing in response to determining that changing the brake operating timing is necessary.

11. The computer-readable non-transitory storage medium storing the computer program including the instructions according to claim 10, further comprising:
determining whether an ending condition that ends an automatic brake control process is satisfied;
determining whether the brake operation is necessary;
updating the determination reference that includes the reference comfort value and the reference stress value; and
in response to determining that the ending condition is not satisfied and that the brake operation is necessary, continue determining whether changing the brake operating timing is necessary from a time after updating a determination reference until determining that the brake operation is unnecessary.

* * * * *